US012592736B2

(12) United States Patent
Besnoff et al.

(10) Patent No.: US 12,592,736 B2
(45) Date of Patent: Mar. 31, 2026

(54) SELF-POWERED BLUETOOTH BACKSCATTER SENSOR SYSTEM

(71) Applicant: North Carolina State University, Raleigh, NC (US)

(72) Inventors: Jordan Besnoff, Raleigh, NC (US); David Ricketts, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 332 days.

(21) Appl. No.: 18/310,303

(22) Filed: May 1, 2023

(65) Prior Publication Data

US 2023/0353181 A1 Nov. 2, 2023

Related U.S. Application Data

(60) Provisional application No. 63/336,430, filed on Apr. 29, 2022.

(51) Int. Cl.
| | |
|---|---|
| *H04B 1/3827* | (2015.01) |
| *A61B 5/00* | (2006.01) |
| *H02J 50/00* | (2016.01) |

(52) U.S. Cl.
CPC ............. *H04B 1/385* (2013.01); *A61B 5/002* (2013.01); *A61B 5/4266* (2013.01); *A61B 5/681* (2013.01);
(Continued)

(58) Field of Classification Search
CPC ............ A61B 5/14532; A61B 5/14546; A61B 5/0022; A61B 5/0002; A61B 5/002;
(Continued)

(56) References Cited

U.S. PATENT DOCUMENTS

| | | | | |
|---|---|---|---|---|
| 10,338,205 | B2 * | 7/2019 | Zhang | ....................... H04B 5/45 |
| 11,457,809 | B1 * | 10/2022 | Biederman | ........... H04W 12/02 |

(Continued)

OTHER PUBLICATIONS

Zhang et al. "FreeRider: Backscatter Communication Using Commodity Radios", Stanford University UCSD.CoNEXT '17 Dec. 12-15, 2017 Incheon, Republic of Korea (Year: 2017).*

*Primary Examiner* — Lester G Kincaid
(74) *Attorney, Agent, or Firm* — Thomas | Horstemeyer, LLP

(57) ABSTRACT

The present disclosure presents self-powered Bluetooth backscatter sensor systems and related methods. One such system comprises a wearable sensor device having communication circuitry, sensor circuitry, and at least one sweat-activated cell for powering the sensor circuitry; and a transmitter device having an interface for receiving power supplied from a power interface of an electronic communication device having a communication receiver. The transmitter device is configured to be powered by the electronic communication device via the power interface and transmit a continuous wave signal, such that the communication circuitry is configured to receive the continuous wave signal. The sensor circuitry is configured to acquire sensor data; and the communication circuitry is configured to modulate the sensor data onto the received continuous wave signal and transmit the modulated signal as a backscattered signal. Accordingly, the communication receiver is configured to receive the transmitted backscattered signal having the modulated sensor data.

14 Claims, 7 Drawing Sheets

(52) U.S. Cl.
CPC ..... *H02J 50/001* (2020.01); *A61B 2560/0219*
(2013.01)

(58) Field of Classification Search
CPC ..... A61B 5/4266; A61B 5/681; A61B 5/6801;
A61B 2560/0209; A61B 2560/0219;
H04W 4/80; H04W 4/38; H04W 12/50;
H04B 1/385
See application file for complete search history.

(56)     References Cited

U.S. PATENT DOCUMENTS

| | | | |
|---|---|---|---|
| 2008/0139894 A1* | 6/2008 | Szydlo-Moore ..... | A61B 5/6833 |
| | | | 600/300 |
| 2011/0187527 A1* | 8/2011 | Goodwill ................. | G08B 1/08 |
| | | | 340/539.13 |
| 2015/0018643 A1* | 1/2015 | Cole .................. | A61B 5/14546 |
| | | | 600/316 |
| 2022/0395198 A1* | 12/2022 | Yu ....................... | H01M 50/121 |

* cited by examiner

112 —
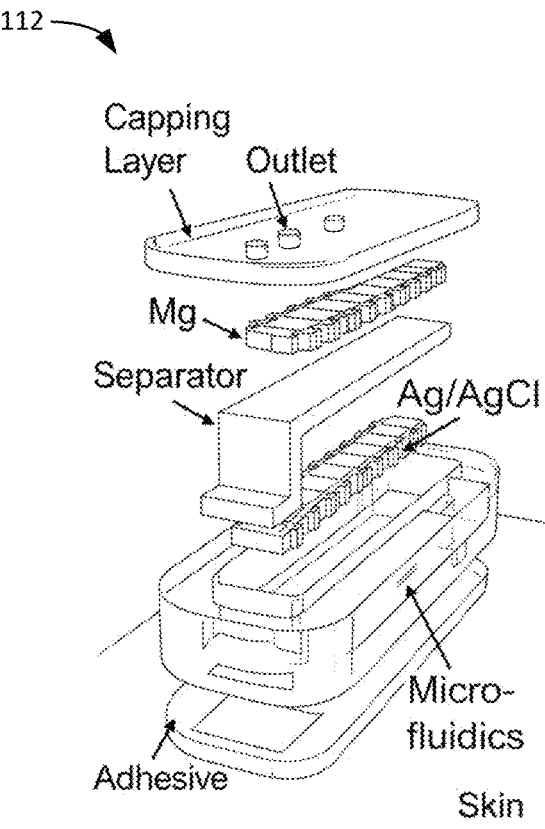
| Size: 21 x 4 x 0.6 mm³ | Battery | Specific Capacity |
|---|---|---|
| Weight: ~75 mg | Coin Cell (CR2032) | 73 Ah/Kg |
| Voltage: 1.5V | Sweat-Powered Battery | 67 Ah/Kg |
FIG. 2
(CONVENTIONAL)

Bluetooth Backscatter Watch Sensor
Vent

Vent

Backscatter Oscillator daughterboard motherboard

Bluetooth Backscatter
Antenna

410

400

400

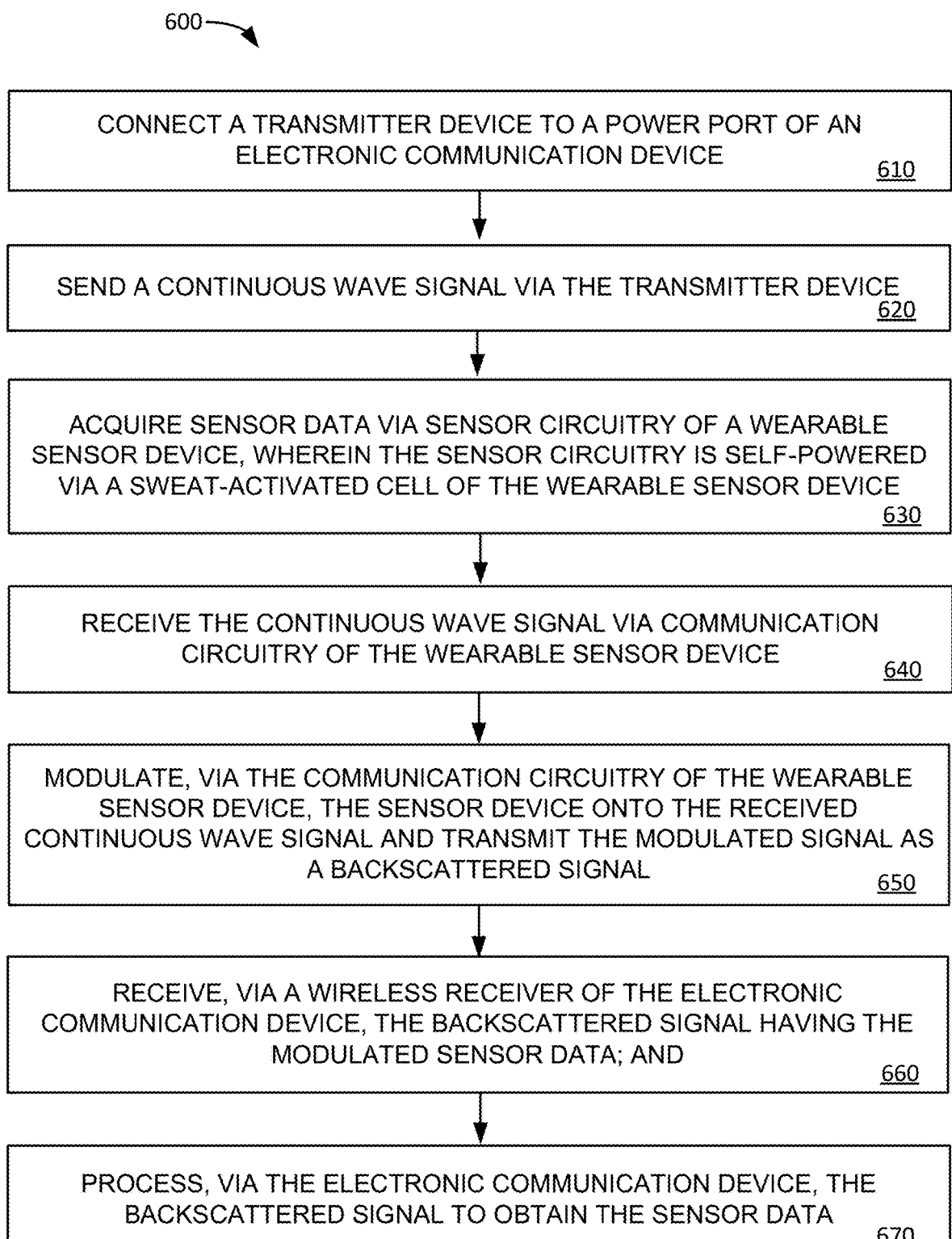

600

CONNECT A TRANSMITTER DEVICE TO A POWER PORT OF AN
ELECTRONIC COMMUNICATION DEVICE
610

SEND A CONTINUOUS WAVE SIGNAL VIA THE TRANSMITTER DEVICE
620

ACQUIRE SENSOR DATA VIA SENSOR CIRCUITRY OF A WEARABLE
SENSOR DEVICE, WHEREIN THE SENSOR CIRCUITRY IS SELF-POWERED
VIA A SWEAT-ACTIVATED CELL OF THE WEARABLE SENSOR DEVICE
630

RECEIVE THE CONTINUOUS WAVE SIGNAL VIA COMMUNICATION
CIRCUITRY OF THE WEARABLE SENSOR DEVICE
640

MODULATE, VIA THE COMMUNICATION CIRCUITRY OF THE WEARABLE
SENSOR DEVICE, THE SENSOR DEVICE ONTO THE RECEIVED
CONTINUOUS WAVE SIGNAL AND TRANSMIT THE MODULATED SIGNAL AS
A BACKSCATTERED SIGNAL
650

RECEIVE, VIA A WIRELESS RECEIVER OF THE ELECTRONIC
COMMUNICATION DEVICE, THE BACKSCATTERED SIGNAL HAVING THE
MODULATED SENSOR DATA; AND
660

PROCESS, VIA THE ELECTRONIC COMMUNICATION DEVICE, THE
BACKSCATTERED SIGNAL TO OBTAIN THE SENSOR DATA
670

FIG. 6

SELF-POWERED BLUETOOTH BACKSCATTER SENSOR SYSTEM

CROSS-REFERENCE TO RELATED APPLICATION

This application claims priority to U.S. provisional application entitled, "Self-Powered Bluetooth Backscatter Sensor System," having Ser. No. 63/336,430, filed Apr. 29, 2022, which is entirely incorporated herein by reference.

BACKGROUND

Typical health monitoring sensor systems have high power requirements. Thus, to overcome power consumption issues, low-power implementations have been introduced that often result in dimensioned communication capabilities, such as having a poor wireless communication range or requiring a physical connection between the sensor device and the receiver/reader component that interferes with practical use of the sensor itself.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 is a diagram of an exemplary sweat-activated cell that can be deployed in an embodiment of the self-powered backscatter sensing system of FIG. 1.

FIG. 6 is a flowchart of a self-powered backscatter sensing method in accordance with various embodiments of the present disclosure.

DETAILED DESCRIPTION

The present disclosure describes various embodiments of self-powered backscatter sensing systems, apparatuses, and related methods.

Figure 1:
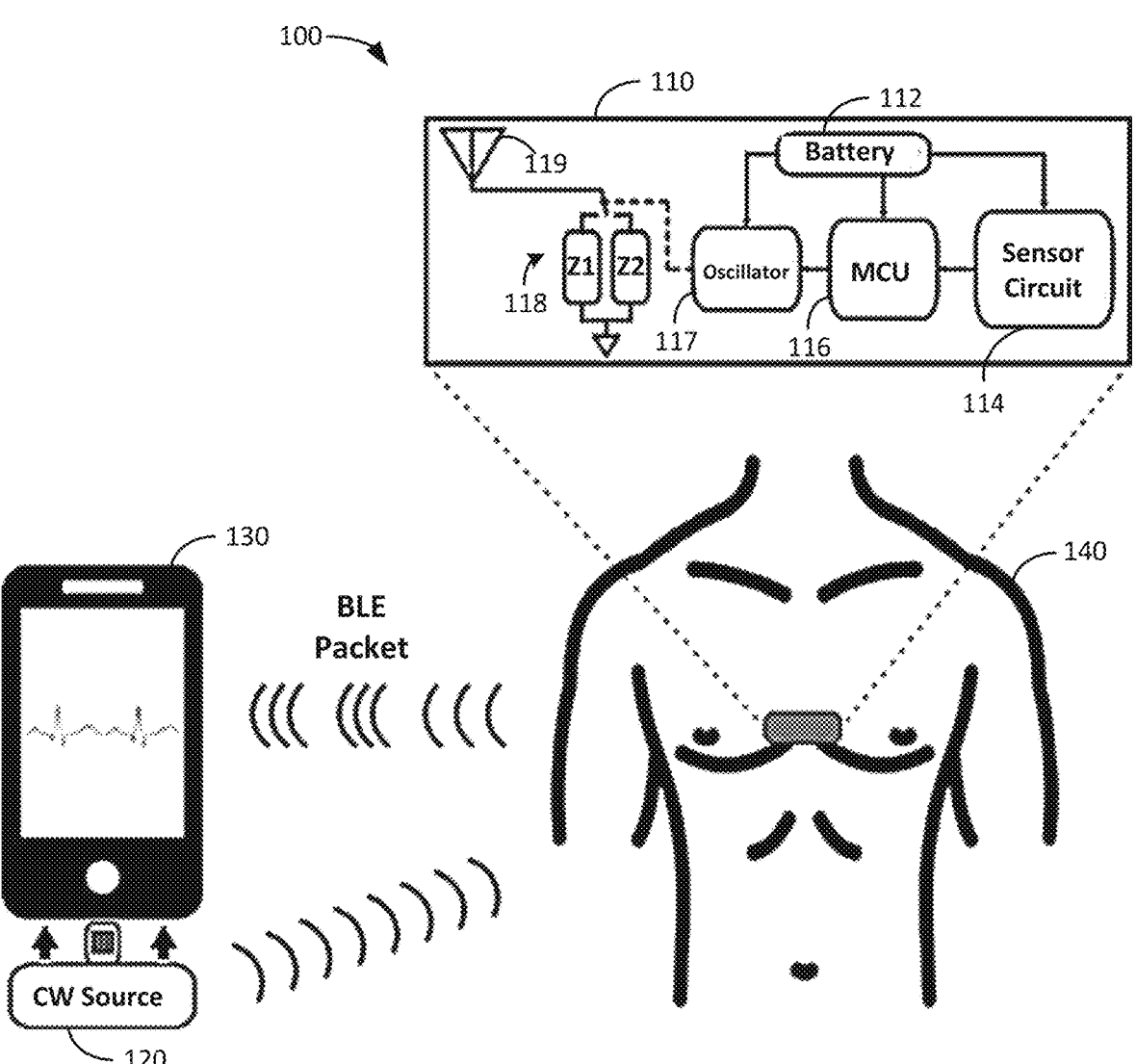
FIG. 1 is a schematic diagram of a self-powered backscatter sensing system in accordance with various embodiments of the present disclosure.

Referring to FIG. 1, an exemplary system 100 of the present disclosure includes a wearable sensor device 110 and a transmitter device 120 that is configured to be coupled to and powered by an electronic communication device 130 having a wireless communication receiver, such as, but not limited to, a smartphone, laptop computer, tablet, etc., having a Bluetooth receiver and a universal serial bus (USB)

port. Correspondingly, the wearable sensor device 110 can be powered by a sweat- or self-activated cell (SAC) ("sweat battery") 112 that is worn on a subject's body and triggered by the subject's perspiration or sweat. The wearable sensor device 110 further features a sensor board having circuitry 114 configured to acquire sensing data (e.g., an electrocardiogram (ECG or EKG) sensor module, etc.) and a microcontroller (MCU) that is self-powered by the sweat-activated cell 112. Further, the wearable sensor device 110 is equipped with communication circuitry comprising an analog oscillator 117, impedance switching circuitry 118, communication antenna 119, etc. that is powered by energy from a received communication signal and/or the sweat-activated cell 112.

In various embodiments, different types of sensor data can be acquired using the sensor circuitry or board 114 of the wearable sensor device 110, such as, but not limited to, heart rate measurements, sweat PH, biochemicals, glucose, hydration indicators, stress indicators, sleep indicators, brain activities, body fluids, electrocardiogram signals, electromyography signals, electroencephalography signals, other physiological signals, etc.

In certain embodiments, one or more electrodes may be connected to the sensor circuitry 114 of the wearable sensor device 110 and be positioned and/or configured to sense, detect, or monitor physiological activity or signals. Accordingly, the MCU 116 of the wearable sensor device 110 may be configured to receive electrical signals as sensor data and record the received electrical signals in a memory and/or transmit the received electrical signals to the transmitter device 120.

In accordance with an exemplary embodiment of the present disclosure, the system 100 operates using backscatter as the wearable sensor 110 modulates the impedance of its antenna 119 in time with the sensor data and reflects an incoming signal created by and transmitted by the transmitter device 120 (as the backscatter illumination source). The sensor device 110 modulates this signal (e.g., selectively changing the amplitude, frequency, and/or phase of the signal) with the sensor data allowing the electronic communication device 130 to receive and process or interpret backscattered reflections of the transmitted signal (to extract the sensor data that was added by the sensor device 110, e.g., in the form of Bluetooth packets) and display the data on a screen of the electronic communication device 130, such as a smartphone, laptop computer, tablet, etc., as indicated in FIG. 1.

Backscatter communication allows the wearable sensor device 110 to operate at much lower frequencies than traditional communication techniques, such as Bluetooth, saving on both power and complexity. An exemplary sensor device 110 operates at approximately 10 MHz and consumes between 1 and 2 mW of power (dependent on the power needs of the specific sensor used). Power is provided to the body-worn sensor device 110 through the sweat-activated cell (SAC) 112 that is able to provide 3V and 5 mAh of capacity with as little as 1 microliter of sweat. Using a single SAC 112, the sensor circuitry 114, which consumes approximately 2 mW, can be powered for about 1.5 hours, in various embodiments. This is sufficiently long for clinical trials and activity monitoring during exercise. In various embodiments, a plurality of SAC's can be cascaded to increase their capacity and voltage. In accordance with the present disclosure, the wearable sensor device 110 is self-powered and does not require a battery, making the sensor maintenance free with a theoretically infinite shelf life.

FIG. 2 shows an exemplary sweat-activated cell 112 that can be deployed in an embodiment of the self-powered backscatter sensing system. This particular example was originally published by Bandodkar et al in Nature Electronics, Vol. 3, pp 554-562 (2020). In this example, the sweat-activated cell 112 can be worn on the skin of a subject via an applied adhesive such that perspiration of the subject is absorbed via microfluidics to a separator separating Ag/AgCl and Mg electrodes, where the perspiration or sweat acts as an electrolyte creating an electrical charge. The sweat-activated cell contains a capping layer with an outlet to permit the release of excess sweat and other byproducts. In this example, the sweat-activated cell has the energy capacity that is similar to that of a coin battery cell.

Figure 3A:
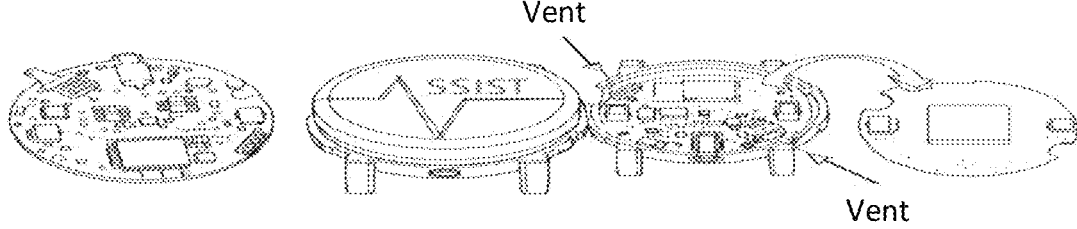
FIGS. 3A-3C show different views of a wearable sensor device of FIG. 1 in the form of a wearable sensor watch.
Figure 3B:
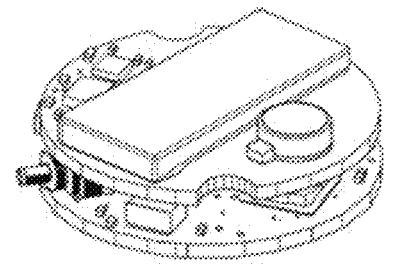
Figure 3C:
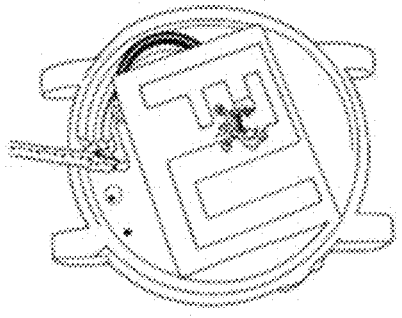

To demonstrate, FIGS. 3A-3C show different views of a wearable sensor device 110 in the form of a wearable sensor watch. The figures show both photographic images and computer model images of a prototype of the wearable sensor device 110 that include images of a printed circuit board of circuitry components (having the requisite backscatter, SAC, and sensor components of FIG. 1) and its placement within a watch case.

Correspondingly, in various embodiments, an exemplary transmitter device 120 is a small portable device having an electrical connector for interfacing a power interface of an electronic communication device 130 that can supply power to the transmitter device, including a smart phone (e.g., having a USB-A port, USB-B port, USB-C port, USB mini port, USB micro port, Lightning port, wireless power interface, general power port, or other type of power interface) that can be connected to the subject's or a nearby person's electronic communication device 130 and power the transmitter device 120. Accordingly, the transmitter device 120 provides a continuous-wave (CW) signal for the wearable sensor 110 to reflect back to the phone 130. This type of system solves the issue of backscatter systems requiring extra large-scale and ubiquitous infrastructure to provide CW signals for sensors to reflect by tapping into a user's electronic communication device, such as a smartphone which already has the capability (e.g., via a Bluetooth transceiver embedded in the device) to receive the backscatter data and is in the vicinity of the wearable sensor device 110 since it is also wearable by or in possession of the subject or a nearby person acquiring the sensor data.

Figure 4A:
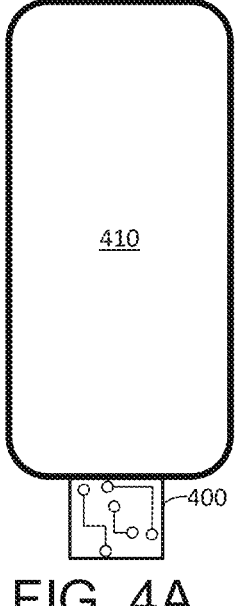
FIG. 4A shows a diagram representation of a prototype of a printed circuit board for the transmitter device of the self-powered backscatter sensing system of FIG. 1.
Figure 4B:
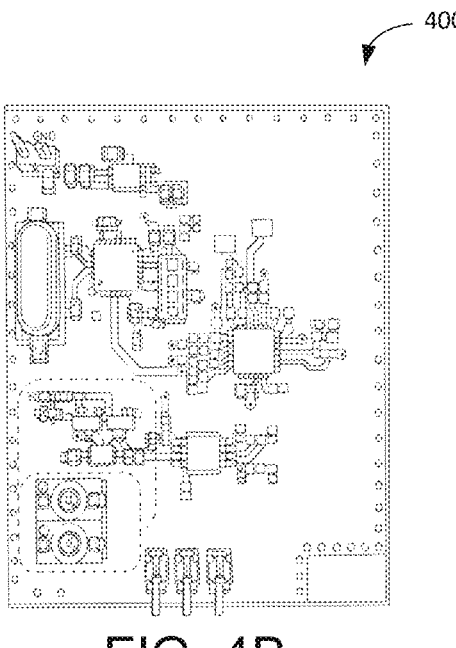
FIG. 4B shows an enlarged image of the transmitter circuitry of FIG. 4A.

Next, FIG. 4A shows a diagram representation of an early prototype of a printed circuit board 400 (approximately 1"×1.5") for the transmitter device 120 that is plugged into a USB port of a smartphone 410, and FIG. 4B shows an enlarged image of the transmitter circuitry 400 of FIG. 4A. During experimental testing, the prototype of the USB connected transmitter 120 consumed approximately 50 mW from the smartphone battery and was tested to have an RF output power of approximately −3.5 dBm.

In an exemplary embodiment, a self-powered backscatter sensing system 100 provides real-time wireless data directly on a user's smartphone 130 without the need for a sensor battery. Thus, the system requires a wearable sensor 110 and a separate small transmitter device 120 (e.g., 1"×1.5") that connects to the user's smartphone 130 via a USB connection that supplies power from the smartphone device 130 to the transmitter device 120. No modifications need to be made to the user's smartphone as the transmitted sensor data is captured through Bluetooth capabilities of the smartphone and displayed on a real-time graph using a microapp installed on the smartphone, in various embodiments.

Figure 5:
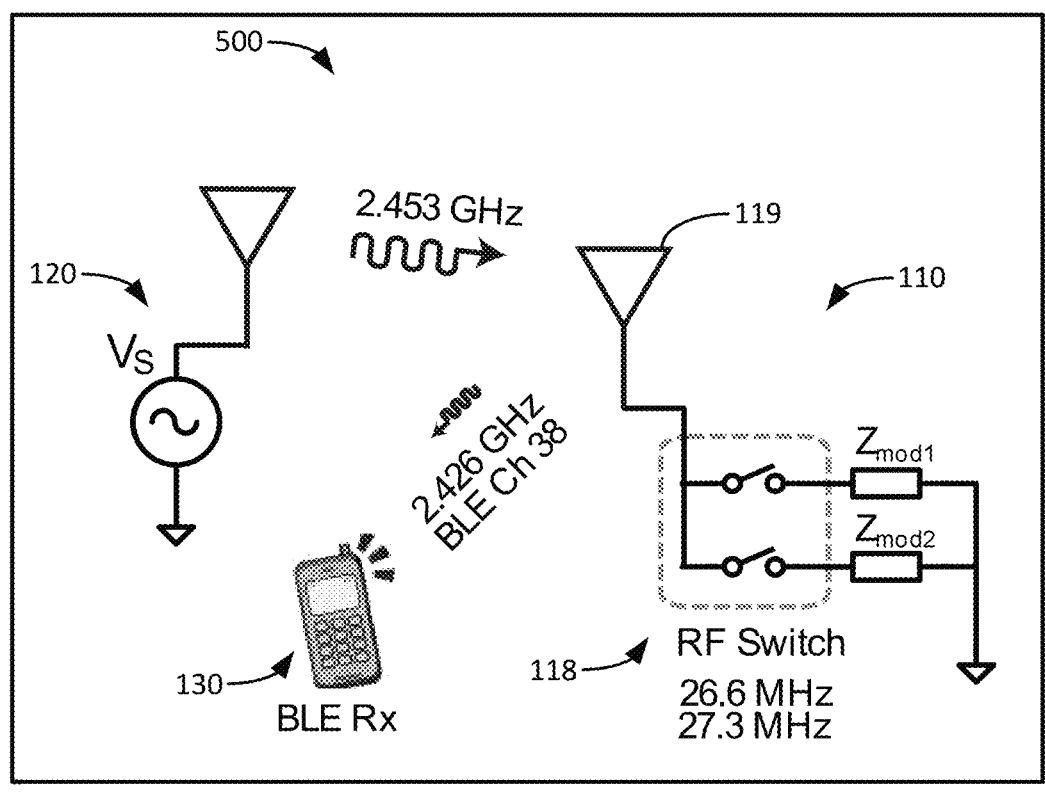
FIG. 5 is a schematic diagram of an exemplary self-powered backscatter sensing system utilizing Bluetooth communications in accordance with various embodiments of the present disclosure.

Referring now to FIG. 5, an exemplary self-powered backscatter sensing system 500 can be configured to sample sensor data and encode the sensor date as backscatter signals in the form of Bluetooth packets (e.g., at a packet data rate of 1 Mbps). In various embodiments, a transmitter 120, in the form of a USB connected device, can be configured to provide a CW signal to be used as the backscatter source, and the wearable sensor device 110 can utilize a cross-coupled oscillator 117 and variable capacitors (not shown) for tuning the backscatter frequencies. In an exemplary implementation, the sensor circuitry 114 or board is tuned to approximately 13.6 MHz and 14.1 MHz, which is <<2.4 GHz, and these 2 frequencies are used to power an RF switch to switch between an open and short to create amplitude modulated backscatter at 2 different frequencies (e.g., 26.6 MHz and 27.3 MHz), representing frequency shift keying (FSK) utilized in Bluetooth communications, in which a low-power microcontroller (MCU) 116 is used to control the RF switch 118. In various embodiments, the transmitter 120 is tuned to 2.453 GHz such that Bluetooth packets that are scattered and reflected via transmissions on one of the channels (e.g., channel 38 at 2.426 GHz) of the Bluetooth specification.

In brief, an exemplary self-powered backscatter sensing system and related method utilizes a battery-free and self-powered sensor device 110 such that it requires no maintenance and has a theoretically infinite shelf life. An exemplary system/method utilizes backscatter to produce Bluetooth packets that can be received and processed by an unmodified smartphone 130. The entire Bluetooth stack and bi-directional communication does not have to be implemented on the sensor device 110 for successful communication, thereby reducing complexity of and saving power consumed by the wearable sensor device 110. While typical Bluetooth sensor systems are power hungry (100's of mW) and rely on traditional communication techniques instead of backscatter, an exemplary self-powered backscatter sensing system 100 takes advantage of communication using reflections which inherently leads to low-power implementations (e.g., a current prototype of an exemplary self-powered backscatter sensing system is 2 mW, where an application-specific integrated circuit (ASIC) can be less than 10 microwatts). The normal disadvantage of reduced range with backscatter communication is negated by using the smartphone as both the transmitter and receiver of backscatter communications, keeping the required communication distance small while also keeping the system power consumption low. Moreover, the typical issue with backscatter systems is the need for extra large-scale and often ubiquitous infrastructure in the form of a single large or multiple CW sources. However, an exemplary self-powered backscatter sensing system 100 can solve such problems by utilizing a smartphone's power source, which is already being utilized to visualize the received sensor data, and using this power to send out a CW signal from a small footprint transmitter device 120. Advantageous uses for such systems and methods of the present disclosure include short-term health & activity monitoring, clinical animal trials, pain/gait monitoring, etc. Additionally, such systems and methods can be used in situations, such as emergency situations in an emergency room, vehicle, and/or in the field, where physical (e.g., tethered or wired) sensor measurements take too long to connect and disconnect, are prone to errors, and/or when time is critical.

Referring now to FIG. 6, a flowchart is presented of a novel self-powered backscatter sensing method 600. The method involves connecting (610) a transmitter device 120 to an external power port or interface of an electronic communication device 130 and sending (620) a continuous wave signal via the transmitter device 120. Further, sensor data is acquired (630) via sensor circuitry 114 of a wearable sensor device 110, wherein the sensor circuitry 114 is self-powered via a sweat-activated cell 112 of the wearable sensor device 110. And, the wearable sensor device 110 receives (640) the continuous wave signal via communication circuitry of the wearable sensor device 110. Correspondingly, the wearable sensor device 110 can modulate, via the communication circuitry of the wearable sensor device 110, the sensor data onto the received continuous wave signal and transmit the modulated signal as a backscattered signal. In turn, a wireless receiver of the electronic communication device 130 can receive (650) the backscattered signal having the modulated sensor data; and the electronic communication device 130 can process the backscattered signal to obtain the sensor data.

Figure 7:
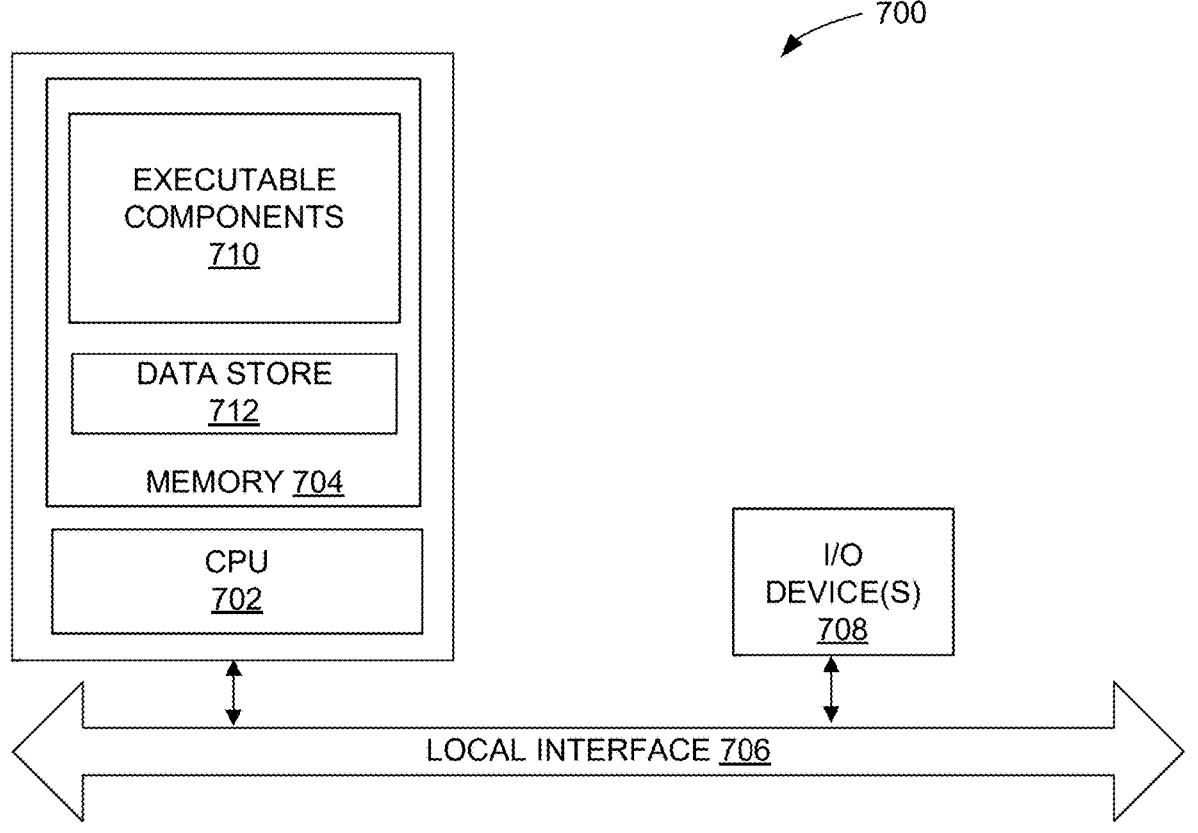
FIG. 7 is a schematic block diagram of a computing device that can be used to implement various embodiments of the present disclosure.

FIG. 7 depicts a schematic block diagram of a computing device 700 that can be used to implement various embodiments of the present disclosure, such as, but not limited to, the electronic communication device 130. An exemplary computing device 700 includes at least one processor circuit, for example, having a processor (CPU) 702 and a memory 704, both of which are coupled to a local interface 706, and one or more input and output (I/O) devices 708. The local interface 706 may comprise, for example, a data bus with an accompanying address/control bus or other bus structure as can be appreciated. The CPU can perform various operations including any of the various operations described herein.

Stored in the memory 704 are both data and several executable components 710 that are executable by the processor 702. Also stored in the memory 704 may be a data store 712 and other data. The data store 712 can include sensor data, and potentially other data. In addition, an operating system may be stored in the memory 704 and executable by the processor 702. The I/O devices 708 may include input devices, for example but not limited to, a touchscreen, communication devices, wearable sensor devices 110, etc. Furthermore, the I/O devices 708 may also include output devices, for example but not limited to, a display, speaker, earbuds, audio output port, a printer, etc.

Certain embodiments of the present disclosure can be implemented in hardware, software, firmware, or a combination thereof. If implemented in software, such logic or functionality, in accordance with embodiments of the present disclosure, are implemented in software or firmware that is stored in a memory and that is executed by a suitable instruction execution system. If implemented in hardware, such logic or functionality can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A system comprising:
a wearable sensor device having communication circuitry, sensor circuitry, and at least one sweat-activated cell for powering the sensor circuitry;
a transmitter device having an interface for receiving power supplied from a power interface of an electronic communication device, wherein the electronic communication device has a communication receiver;
wherein the transmitter device is configured to be powered by the electronic communication device via the power interface and transmit a continuous wave signal;
wherein the communication circuitry of the wearable sensor device is configured to receive the continuous wave signal;
wherein the sensor circuitry of the wearable sensor device is configured to acquire sensor data;
wherein the communication circuitry is configured to modulate the sensor data onto the received continuous wave signal and transmit the modulated signal as a backscattered signal; and
wherein the communication receiver of the electronic communication device is configured to receive the transmitted backscattered signal having the modulated sensor data.

2. The system of claim 1, wherein the sweat-activated cell operates using sweat perspiration of a wearer of the wearable sensor device.

3. The system of claim 1, wherein the transmitted backscatter signal is transmitted over a Bluetooth channel.

4. The system of claim 1, wherein the sensor data comprises heart rate sensor data measurements, sweat PH sensor data, biochemical sensor data, glucose sensor data, hydration sensor data, stress sensor data, brain sensor data, electrocardiogram sensor data, electromyography sensor, or electroencephalography sensor data.

5. The system of claim 1, wherein the electronic communication device comprises a smartphone.

6. The system of claim 1, wherein the power interface comprises a USB port.

7. The system of claim 1, wherein the communication circuitry is powered by the at least one sweat-activated cell.

8. The system of claim 1, wherein the communication circuitry is powered by the received continuous wave signal.

9. A method comprising:
connecting a transmitter device to a power interface of an electronic communication device;
sending a continuous wave signal via the transmitter device;
acquiring sensor data via sensor circuitry of a wearable sensor device, wherein the sensor circuitry is self-powered via a sweat-activated cell of the wearable sensor device;
receiving the continuous wave signal via communication circuitry of the wearable sensor device;
modulating, via the communication circuitry of the wearable sensor device, the sensor data onto the received continuous wave signal and transmitting the modulated signal as a backscattered signal;
receiving, via a wireless receiver of the electronic communication device, the backscattered signal having the modulated sensor data; and
processing, via the electronic communication device, the backscattered signal to obtain the sensor data.

10. The method of claim 9, wherein the transmitted backscatter signal is transmitted over a Bluetooth channel.

11. The method of claim 9, wherein the electronic communication device comprises a smartphone.

12. The method of claim 9, wherein the sensor data comprises heart rate sensor data measurements, sweat PH sensor data, biochemical sensor data, glucose sensor data, hydration sensor data, stress sensor data, brain sensor data, electrocardiogram sensor data, electromyography sensor, or electroencephalography sensor data.

13. The method of claim 9, wherein the communication circuitry is powered by the sweat-activated cell.

14. The method of claim 9, wherein the communication circuitry is powered by the received continuous wave signal.

\* \* \* \* \*